United States Patent [19]
Monget

[11] Patent Number: 5,330,889
[45] Date of Patent: Jul. 19, 1994

[54] PROCESS AND MEDIUM FOR IDENTIFICATION OF BACTERIA OF THE LISTERIA GENUS

[75] Inventor: Daniel Monget, Saint-Sorlin en Bugey, France

[73] Assignee: Bio Merieux, France

[21] Appl. No.: 819,876

[22] Filed: Jan. 13, 1992

[30] Foreign Application Priority Data

Jan. 16, 1991 [FR] France ............... 91 00650

[51] Int. Cl.$^5$ .............. C12Q 1/04; C12Q 1/37; G01N 21/75
[52] U.S. Cl. ........................ 435/34; 435/24; 435/810; 436/166
[58] Field of Search ............ 435/34, 24, 810; 436/166

[56] References Cited

U.S. PATENT DOCUMENTS 4,208,480 6/1980 D'Amato ............... 435/34
4,874,695 10/1989 Pincus ............... 435/19

OTHER PUBLICATIONS

F. del Corral et al., "Evaluation of the API-ZYM System for Identification of Listeria", Food Microbiology, vol. 7, No. 2, 1990, pp. 99–106.

P. A. Kramer et al., "Media Selective for Listeria Monocytogenes", J. Appl. Bact., vol. 32, 1969, pp. 381–394.

Kampfer P., Differentiation of Cornne Bacterium . . . J of Clinical Micro vol. 30 #5 May 1992 pp. 1067–1071.

*Primary Examiner*—Michael G. Wityshyn
*Assistant Examiner*—Ralph G. Tomer
*Attorney, Agent, or Firm*—Oliff & Berridge

[57] ABSTRACT

The invention relates to a process of bacteriological analysis for differentiating the pathogenic *monocytogenes* species in a sample which may contain bacteria of the listeria genus, a medium for its implementation and a device for identifying *Listeria monocytogenes*. The process consists in bringing the sample to be analyzed into contact with an identification medium comprising a chromogenic or fluorigenic substrate capable of being hydrolyzed by glycine aminopeptidase.

18 Claims, No Drawings

PROCESS AND MEDIUM FOR IDENTIFICATION OF BACTERIA OF THE LISTERIA GENUS

FIELD OF THE INVENTION

The subject of the present invention is a process and a medium for bacteriological identification enabling the various species of the Listeria genus to be differentiated and/or identified. More specifically, the main subject of the invention is the differentiation of the pathogenic *monocytogenes* species from the other non-pathogenic species of the Listeria genus.

PRIOR ART

The Listeria genus today comprises seven species of which only *Listeria monocytogenes* is pathogenic for man. Microorganisms are the cause of severe epidemics in man following contaminations caused by food. Two species of Listeria are mainly isolated from foodstuffs (mainly milk and milk products): *Listeria innocua*, non-pathogenic and *Listeria monocytogenes*, pathogenic.

These two species have numerous biochemical characteristics in common and it is therefore difficult to differentiate between them. The tests currently used are as follows.

1) The β-hemolysis test: this test is based on the determination of a β-hemolytic activity linked to the production by the bacterium of a substance which causes the lysis of erythrocytes (listeriolysine). This test is carried out on sheep or horse blood agar, but the response is often discreet. This test is therefore not very reliable and while it enables the two species mainly encountered to be differentiated, namely *L. monocytogenes* (positive response) from *L. innocua* (negative response), it is not specific for the pathogenic species.

2) The CAMP test: this test is combined with the β-hemolysis test described above. The test is carried out on trypticase soya bean agar containing 5% washed sheep erythrocytes. The β-hemolytic strain of *S. aureus*, CIP 5710, is inoculated in a streak perpendicular to the streaks formed by the culture of the Listeria strain to be tested. The intensification of the hemolysis by the staphylococcus in contact with the two zones indicates a positive reaction. In practice, the CAMP test is a difficult technique to implement, and, like hemolysis, is not always very reliable.

SUMMARY OF THE INVENTION

The main subject of the present invention is therefore a method for differentiating the *monocytogenes* species of the Listeria genus, which is particularly selective, sensitive and relatively not very subjective.

Secondly, the subject of the present invention is a complete system for identifying the various species of the Listeria genus.

After subjecting the seven species of the Listeria genus to examination using more than 500 different biochemical tests consisting of:

142 enzymatic tests (peptidases, oxidases, phosphatases, esterases and the like)

82 fermentation tests 278 auxanogram tests, the Applicant arrived at the fundamental discovery according to which all the Listeria species possessed a glycine aminopeptidase enzymatic activity, with the exception of the pathogenic species *L. monocytogenes*.

From this discovery, the present invention therefore proposes a particularly selective process of bacteriological analysis for the species of the Listeria genus and consisting in bringing the sample to be analyzed into contact, under incubation, with an identification medium comprising a glycine aminopeptidase substrate which is chromogenic or fluorigenic and which is capable of being hydrolyzed in the presence of the aforementioned enzyme.

Still from the same discovery, the invention proposes a medium for the bacteriological identification of the species of the Listeria genus, for example packaged in dehydrated form, comprising a glycine aminopeptidase substrate which is homogenic or fluorigenic, and which is capable of being hydrolyzed in contact with or in the presence of the sample to be analyzed, which may contain the *L. monocytogenes* species.

For the purpose of characterizing Listeria species other than *monocytogenes*, such a medium may also comprise one or more conversion substrates which make it possible to characterize the species present in the sample to be analyzed. They are preferably chosen from the following substrates:

bacteria-fermentable substrates, that is to say carbohydrates (D-xylose, ribose, rhamnose, tagatose, α-methyl-D-mannoside, α-methyl-D-glucoside, mannitol and the like)

bacteria-reducible substrates such as nitrates and preferably potassium nitrate, enzyme-hydrolyzable substrates such as α-mannosidase substrates.

Chromogenic or fluorigenic substrate is understood as meaning any marker whose molecule, in the presence of at least one specific enzyme, is capable of being hydrolyzed or cut into two parts, namely a non-chromogenic or non-fluorigenic inert part and a chromogenic or fluorigenic part which can develop a color visible to the naked eye or under UV light, directly or indirectly, that is to say by the action of an additional chemical compound called indicator.

Thus, the chromogenic or fluorigenic substrate may be chosen from the substrates which can be hydrolyzed to form a product:

which is directly fluorigenic, namely glycine-7-amido-4-methylcoumarin, glycine-7-amido-4-trifluoromethylcoumarin, which is directly chromogenic, namely glycine-4-nitroanilide, and which is indirectly chromogenic, namely glycine-2-naphthylamide and glycine-4-methoxy-2-naphthylamide, to which is added an indicator chosen from the diazonium salts of the Fast Blue BB type, and para-dimethylaminocinnamaldehyde.

A colored complex is thus obtained in the presence of a positive reaction. Naturally, the above substrates are given only by way of example and do not constitute a limitation of the present invention.

The concentration of the glycine aminopeptidase substrate introduced into the medium varies preferably between 0.01 mM and 10 mM.

The medium according to the invention comprises a buffer system chosen from Tris, phosphate buffers and peptone media. It enables the pH of the medium to be adjusted to a value between 6 and 9.

According to a particular formulation of the medium of the invention, the medium contains sodium chloride for a content preferably between 0 and 10 g. It may also contain at least one activator of glycine aminopeptidase in an amount preferably between 0 and 100 mg per l litre of medium and preferably chosen from the bivalent cations $Mg^{2+}$, $Ca^{2+}$, $Mn^{2+}$ and the like. According to this particular formulation, the medium may contain a solution of $MnCl_2$ or $MnSO_4$, preferably in an amount of 30 mg/l of medium.

The preparation of the medium according to the invention, the implementation of the process and the advantages are now illustrated by the following examples.

EXAMPLE 1

Preparation of a Medium According to the Invention

A preferred formulation of the medium is as follows:

| | | |
|---|---|---|
| glycine-2-naphthylamide | 0.65 g | |
| trizma base | 6.06 g | |
| NaCl | 5.00 g | |
| distilled water | 1 l | |
| HCl | qs pH 8 | |

The preceding formulation is dehydrated in microtiter-plate wells by ventilated drying at 37° C. for 24 hours. The volume of the medium to be evaporated is 100 microliters per well. The media thus prepared are stored under a dehydrating agent in darkness at +4° C. up to their use.

EXAMPLE 2

Implementation of the Process According to the Invention

The implementation below is given by way of example. It is obvious that it can undergo numerous variations.

Using an isolate on sheep blood Columbia agar (5%), a suspension of the Listeria strain to be studied is prepared in sterile distilled water. This suspension is adjusted to the No. 4 point of the McFarland scale. One hundred microliters of this suspension are introduced into a well of the microtiter plate containing the dehydrated formulation described according to Example 1. After incubating for 4 hours at 37° C., a drop of Fast Blue BB reagent is added to the reaction medium in order to detect the presence of free 2-naphthylamine. The development of an orange color indicates a positive reaction.

EXAMPLE 3

Use of the Medium According to the Invention to Differentiate the Two Listeria Species, *L. monocytogenes* and *L. innocua*

The implementation of the process according to Example 2 is applied to the differentiation of the following strains:

41 *L. monocytogenes* strains
33 *L. innocua* strains.

The results obtained were as follows, expressed as the number of positive strains:

*L. monocytogenes*: 0/41, or 0%
*L. innocua*: 33/33, or 100%

This example demonstrates the specificity of the medium and its reliability resulting from an observation which is not subject to any confusion.

EXAMPLE 4

Use of a Medium According to the Invention in Combination With Other Detection Media to Identify the Species of the Listeria Genus.

The detection media chosen, combined with the medium according to the invention, which are only an illustration of the possibilities offered, are the following media:

detection medium for bacteria which ferment D-xylose
detection medium for bacteria which ferment ribose
detection medium for bacteria which ferment α-methyl-D-mannoside
detection medium for bacteria which reduce nitrates.

The formulation of each of the media is as follows:
medium according to the invention, or A, formulation according to Example 1
medium comprising the fermentable carbohydrate, or B

| | |
|---|---|
| distilled water | 1000 ml |
| carbohydrate: D-xylose, ribose, α-Me-D-mannoside | 10 g |
| bacto-peptone Difco | 5 g |
| phenol red | 60 mg |
| pH adjusted to | 8.5 | medium comprising nitrates, or C

| | |
|---|---|
| distilled water | 1000 ml |
| potassium nitrate | 1 g |
| bacto-peptone Difco | 10 g |
| pH adjusted to | 7.0 |

The various formulations were sterilized by filtration on a 0.22-micron filter and distributed in microtiter-plate wells alongside the glycine aminopeptidase test described above in an amount of 100 microliters per well. The reaction media were then dehydrated by ventilated drying at 37° C. for 24 hours.

The series of tests thus prepared were stored under a dehydrating agent, in darkness and at +4° C. up to their use. 104 Listeria strains were studied, distributed as follows:

41 *L. monocytogenes*
33 *L. innocua*
8 *L. ivanovii*
3 *L. welshimeri*
14 *L. seeligeri*
3 *L. grayi*
2 *L. murrayi*.

These various strains were tested in the following manner:

for each strain isolated on sheep blood Columbia agar (5%), a bacterial suspension was prepared in sterile distilled water
this suspension was adjusted to the No. 4 point of the McFarland scale
100 microliters were distributed to the wells corresponding to the 5 media described above
after incubating for 4 hours at 37° C., the various reactions were interpreted in the following manner:
medium A: (see Example 3)
medium B:
yellow coloration: positive reaction red coloration: negative reaction medium C: after adding a drop of each of the reagents NIT1 and NIT2, marketed by BIO MERIEUX and consisting, in a solution in acetic acid, of sulfanilic acid and N,N-dimethyl-1-naphthylamine respectively red coloration: positive reaction no coloration: negative reaction The results obtained were as follows:

|  | Medium | | | | |
| --- | --- | --- | --- | --- | --- |
|  | A | B | | C | |
|  | Substrate | | | | |
| Species | Glycine amino- peptidase substrate | D- xylose | Ribose | alpha- methyl D- manno- side | nitrate |
| L. monocytogenes | − | − | − | + | − |
| L. innocua | + | − | − | + | − |
| L. ivanovii | + | + | + | − | − |
| L. welshimeri | + | + | − | + | − |
| L. seeligeri | + | + | − | − | − |
| L. grayi | + | − | + | + | − |
| L. murrayi | + | − | + | + | + |

−: 0% of positive reaction
+: 100% of positive reaction

This table shows that the seven species composing the Listeria genus are all separated two-by-two by at least one of the five selected media.

This combination of medium makes it possible to identify any Listeria strain simply and precisely whatever the species to which it belongs.

What is claimed is:

1. A process of bacteriological analysis in which the sample to be analyzed is brought into contact with an identification medium comprising a chromogenic or fluorigenic substrate capable of being hydrolyzed in the presence of at least one enzyme associated with the metabolism of at least one bacterial species, wherein, in order to differentiate the *monocytogenes* species in a sample which may contain bacteria of the Listeria genus, a glycine aminopeptidase substrate is introduced into the identification medium.

2. The process as claimed in claim 1, wherein the concentration of the glycine aminopeptidase substrate ranges between 0.01 mM and 10 mM.

3. The process as claimed in claim 2, wherein a buffer system is introduced with the substrate in order to adjust the pH to a value between 6 and 9.

4. The process as claimed in claim 1 wherein at least one glycine aminopeptidase activator is introduced into the identification medium.

5. The process as claimed in claim 4, wherein the activator is a bivalent cation selected from the group consisting of $Mn^{++}$, $Mg^{++}$ and $Ca^{++}$.

6. A medium for bacteriological identification, comprising a chromogenic or fluorigenic substrate capable of being hydrolyzed in the presence of at least one enzyme associated with the metabolism of at least one bacterial species, wherein, in order to differentiate the *monocytogenes* species in a sample to be analyzed brought into contact with the said medium and which may contain bacteria of the Listeria genus, the medium comprises a glycine aminopeptidase substrate.

7. The medium as claimed in claim 6, wherein the substrate is directly fluorigenic and is glycine-7-amido-4-methylcoumarin or glycine-7-amido-4-trifluoromethyl-coumarin.

8. The medium as claimed in claim 6, wherein the substrate is directly chromogenic and is glycine-4-nitroanilide.

9. The medium as claimed in claim 6, wherein the substrate is made chromogenic by adding an indicator and is glycine-2-naphthylamide or glycine-4-methoxy-2-naphthylamide.

10. The medium as claimed in claim 9, wherein the indicator is a diazonium salt or para-dimethylaminocinnamaldehyde.

11. The medium as claimed in claim 6, wherein the medium comprises a buffer system for maintaining its pH between 6 and 9.

12. The medium as claimed in claim 6, wherein the molar concentration of the substrate is between 0.01 mM and 10 mM.

13. The medium as claimed in claim 6, wherein the medium further comprises sodium chloride and at least one glycine aminopeptidase activator.

14. The medium as claimed in claim 13, wherein the activator is a bivalent cation selected from the group consisting of $Mn^{++}$, $Mg^{++}$ and $Ca^{++}$.

15. The medium as claimed in claim 14, wherein the amount of activator is up to 100 mg per 1 liter.

16. The medium as claimed in claim 6, wherein the medium is dehydrated.

17. The medium as claimed in claim 10, wherein the diazonium salt is Fast Blue BB.

18. The medium as claimed in claim 6, wherein the medium further comprises at least one conversion substrate whose chemical conversion makes possible characterization of the Listeria species present in the sample to be analyzed, wherein the at least one conversion substrate is selected from the group consisting of (A) fermentation substrates selected from the group consisting of D-xylose, ribose, alpha-methyl-mannoside, rhamnose, tagatose, alpha-methyl-D-glucoside and mannitol, (B) potassmium nitrate reducible substrates, and (C) alpha-mannosidase enzyme substrates.

* * * * *